US012567490B2

(12) United States Patent
Weissman et al.

(10) Patent No.: US 12,567,490 B2
(45) Date of Patent: Mar. 3, 2026

(54) DEEP-LEARNING-BASED MEDICAL IMAGE INTERPRETATION SYSTEM FOR ANIMALS

(71) Applicant: Yoy Ishta Nem, Inc., Wilmington, DE (US)

(72) Inventors: Alan Weissman, Oakland, CA (US); Andrew Weissman, Red Bank, NJ (US)

(73) Assignee: Yoy Ishta Nem, Inc., Wilmington, DE (US)

( * ) Notice: Subject to any disclaimer, the term of this patent is extended or adjusted under 35 U.S.C. 154(b) by 283 days.

(21) Appl. No.: 17/960,792

(22) Filed: Oct. 5, 2022

(65) Prior Publication Data

US 2023/0108955 A1     Apr. 6, 2023

Related U.S. Application Data

(60) Provisional application No. 63/252,548, filed on Oct. 5, 2021.

(51) Int. Cl.
G16H 15/00          (2018.01)
G16H 50/20          (2018.01)

(52) U.S. Cl.
CPC ............. G16H 15/00 (2018.01); G16H 50/20 (2018.01)

(58) Field of Classification Search
CPC .............................. G16H 15/00; G16H 50/20
USPC ........................................................ 705/2–3
See application file for complete search history.

(56) References Cited

U.S. PATENT DOCUMENTS

| | | | | |
|---|---|---|---|---|
| 9,589,374 | B1 * | 3/2017 | Gao ..................... | A61B 6/5211 |
| 12,178,560 | B2 | 12/2024 | Wallack et al. | |
| 2007/0143149 | A1 * | 6/2007 | Buttner .................. | G16H 10/60 705/3 |
| 2010/0198755 | A1 * | 8/2010 | Soll ........................ | G16H 10/60 706/11 |
| 2011/0119212 | A1 * | 5/2011 | De Bruin ............... | A61B 5/369 706/12 |
| 2016/0267221 | A1 * | 9/2016 | Larcom .................. | G16H 70/00 |
| 2016/0267222 | A1 * | 9/2016 | Larcom .................. | G16H 30/20 |
| 2019/0197358 | A1 * | 6/2019 | Madani ................. | A61B 6/5217 |
| 2020/0167911 | A1 * | 5/2020 | Park .......................... | G06T 7/11 |
| 2021/0035015 | A1 * | 2/2021 | Edgar ................... | G06F 18/211 |
| 2021/0035289 | A1 * | 2/2021 | Zedayko ............... | G16H 30/20 |
| 2021/0151137 | A1 * | 5/2021 | Zedayko ............... | G16H 20/30 |
| 2021/0398676 | A1 * | 12/2021 | Evans .................... | G16H 30/40 |
| 2021/0407086 | A1 * | 12/2021 | Liu ........................ | G06N 3/096 |
| 2022/0051114 | A1 * | 2/2022 | Lyman ................... | G16H 50/20 |
| 2022/0318995 | A1 * | 10/2022 | Chen ...................... | G16H 50/20 |
| 2023/0005600 | A1 * | 1/2023 | Hoelzer ................ | G16H 50/20 |
| 2023/0062811 | A1 * | 3/2023 | Kunz .................... | G16H 30/40 |

* cited by examiner

*Primary Examiner* — Michael Tomaszewski
(74) *Attorney, Agent, or Firm* — Shield Intellectual Property PC; Kirk D. Wong

(57)          ABSTRACT

A deep-learning-based medical image interpretation system and method uses one or more neural network models to analyze medical images of animals. Result sets from the one or more neural network models are used to create one or more medical diagnoses. One or more treatment options are generated in response to the one or more medical diagnoses. One or more animal products may be suggested related to care of the one or more medical diagnoses.

17 Claims, 6 Drawing Sheets

500

DEEP-LEARNING-BASED MEDICAL IMAGE INTERPRETATION SYSTEM FOR ANIMALS

PRIORITY CLAIM

This application claims benefit under 35 U.S.C. § 119(e) of Provisional Application No. 63/252,548 filed Oct. 5, 2021 the entire contents of which is hereby incorporated by reference as if fully set forth herein.

TECHNICAL FIELD

This disclosure relates generally to the use of artificial neural networks for analyzing data and making predictions based upon the data, and more particularly, a system that uses deep learning to enable the automated analysis of medical images and other data of animals to generate diagnostic predictions for medical purposes.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

At this point in history, it is possible for many professional people to naively apply machine learning to medical imaging, for instance, using sample code and data sets that are widely available on many websites and blogs. However, upon further investigation by a qualified professional, one will invariably find that any seemingly positive results presented in even the best academic papers will not meet real-world expectations. This is often based on some combination of a) model overfitting leading to poor real-world results, h) reporting Validation-Set results as if they are real-world results, c) non-generalizable results for the necessary Sensitivity/Specificity of real-world application, or d) only apply to a singular or small subset of patient conditions or use cases. Additionally, due to the far-reaching implications that Artificial Intelligence (AI) and Machine Learning (ML) systems have on individuals and industries, even a highly effective system should be considered substandard without unique and necessary innovation to the design and human interaction of the system in a way that drives both user satisfaction and real-world operating improvements. Furthermore, because medicine is an advancing field with numerous new conditions and treatment options appearing, a thorough AI system is uniquely necessary to serve the needs of patient, vet, and owner alike.

BRIEF DESCRIPTION OF THE DRAWINGS

The numerous advantages of the present invention may be better understood by those skilled in the art by reference to the accompanying figures in which.

DETAILED DESCRIPTION

Figure 1:
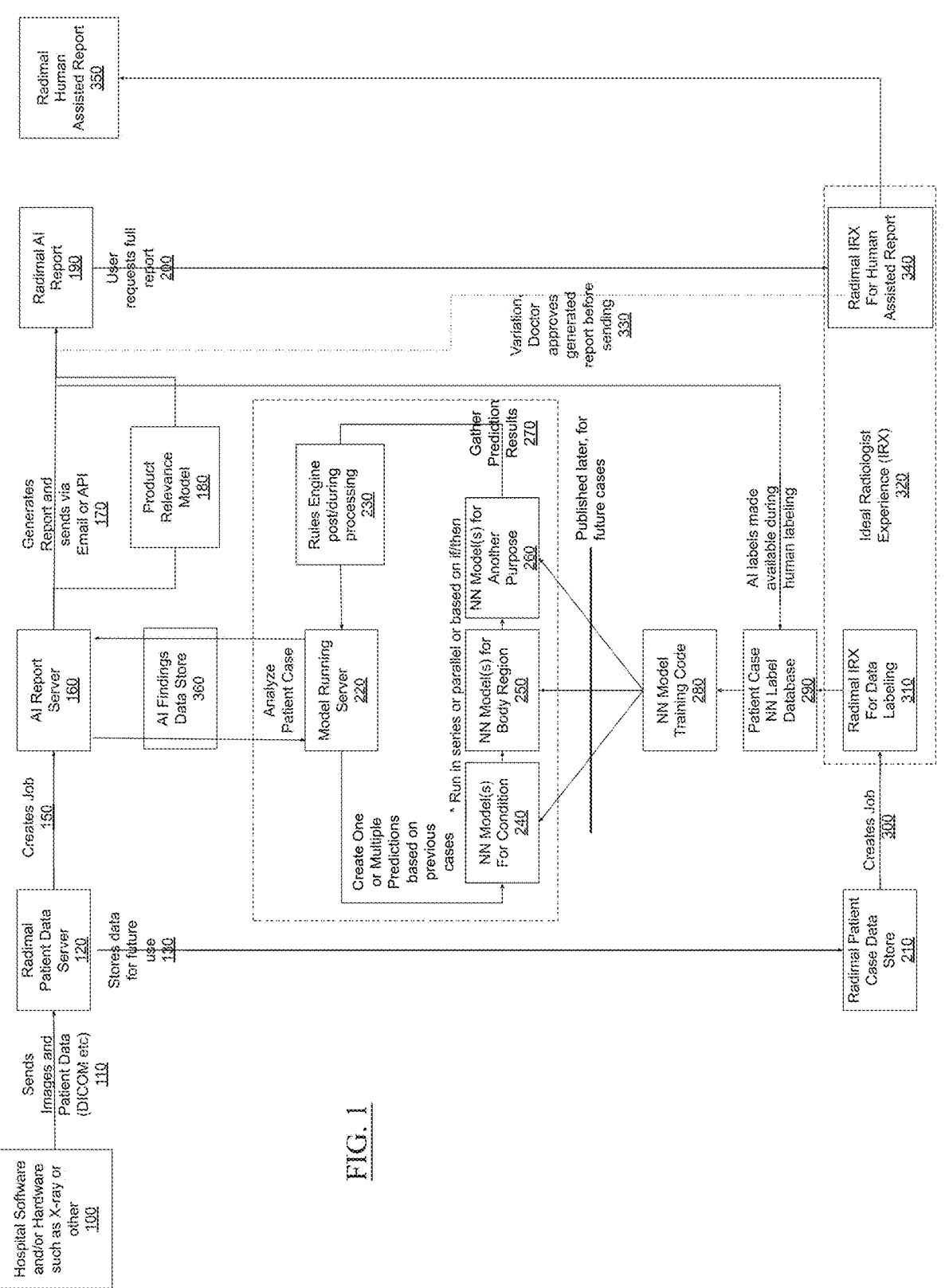
FIG. 1 is a schematic diagram of an example computing environment in accordance with example embodiments.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein according to the following outline:

1.0. General Overview
2.0. Operating Environment
3.0. Implementation Mechanisms—Hardware Overview
4.0. Extensions and Alternatives

1.0. General Overview

This overview presents a basic description of some aspects of possible embodiments of the present invention. It should be noted that this overview is not an extensive or exhaustive summary of aspects of the possible embodiment. Moreover, it should be noted that this overview is not intended to be understood as identifying any particularly significant aspects or elements of the possible embodiment, nor as delineating any scope of the possible embodiment in particular, nor the invention in general. This overview merely presents some concepts that relate to the example possible embodiment in a condensed and simplified format and should be understood as merely a conceptual prelude to a more detailed description of examples and possible embodiments that follows below.

Embodiments of the present invention provide for non-invasive methods, diagnostic tests, and computer-implemented machine learning methods, apparatuses, and systems for assessing a likelihood that a patient has a disease.

Medical images are largely interpreted by medical practitioners, but these interpretations can be subjective, affected by the level of the physician's experience in the field and/or work environment conditions such as pressure to generate interpretations quickly, etc. Image analysis via machine learning can support a healthcare practitioner's workflow.

As used herein "machine learning" refers to algorithms that give a computer the ability to learn without being explicitly programmed including algorithms that learn from and make predictions about data. Machine learning algorithms include, but are not limited to, decision tree learning, artificial neural networks (ANN) (also referred to herein as a "neural net"), deep learning neural networks, support vector machines, rule-based machine learning, random forest, etc. The machine learning process has the ability to continually learn and adjust the model as new data becomes available and does not rely on explicit or rules-based programming. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech, images, and text.

Learned observable features include objects and quantifiable regularities learned by the machine during supervised learning. A machine provided with a large set of well-classified data is better equipped to distinguish and extract the features pertinent to successful classification of new data. An example deep learning neural network can be trained on a set of expert classified data. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., making the model available to receive "real world" data, etc.). During operation, neural network classifications can be confirmed or denied (e.g., by an expert user, expert system, reference database, etc.) to continue to improve neural network behavior. The example neural network is then in a state of active learning, as parameters for classification that determine neural network behavior are updated based on ongoing interactions.

A deep learning machine that utilizes active learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation. Deep learning machines can utilize active learning when interacting with physicians to counteract the small dataset available in the supervised training. These deep learning machines can improve their computer-aided diagnosis over time through training and active learning.

In an embodiment, the machine learning algorithms are "trained" by building a model from inputs or "labels." Those inputs may be retrospective data with a known diagnosis and data from clinical factors of those patients. In that instance the model, the trained machine learning algorithm, can, for example, classify new patient data into a category indicative of a likelihood of having cancer or into another category indicative of a likelihood of not having cancer. The category indicative of a likelihood of having cancer can be further divided into qualitative or quantitative sub-groups. Those qualitative groups may include identifiers such as low, medium, intermediate, high, or a combination thereof for a likelihood of having cancer. The quantitative groups may include identifiers such as a percentage, multiplier value, risk score, composite score or any numerical value that can be provided to the user for indicating the likelihood of having cancer. Those quantitative and qualitative groups may also be presented in a table, such as a "risk categorization table."

Embodiments provide a data acquisition and processing method, apparatus and system to automate analysis of medical images and other data of animals to generate diagnostic predictions for medical purposes.

In an embodiment, a system for a data acquisition engine collects medical images of animal patients, along with other patient data, such as date of birth, breed, the results of other tests, hospital/doctor information such as treatment dates, doctors, and other information, from various sources.

An embodiment provides facilities for the labeling and classification of the aforementioned data by a medical doctor or other expert who assigns one or more labels as mentioned above to identify various aspects of each image/case. This example method prepares the information for the training and deployment of a deep learning network.

An embodiment creates, trains and deploys a deep learning network, including preparation, preprocessing and training of the labeled and classified data. An example method includes unique combinations of models running separately or together to generate analysis.

An embodiment implements a neural network to analyze patient data and generate reports or other information pertinent to a specific animal.

2.0. Operating Environment

Data Acquisition

Referring to FIG. 1, in an embodiment, imaging devices (e.g., gamma camera, positron emission tomography (PET) scanner, computed tomography (CT) scanner, X-ray machine, magnetic resonance (MR) imaging machine, ultrasound scanner, etc.) 100 generate medical images (e.g., native Digital Imaging and Communications in Medicine (DICOM) images, etc.), which may contain numerous details of body structures or tissues and identifying such details may assist a veterinarian with relevant diagnosis.

This Data Acquisition step 100 is unique to animal medicine in that the amount, type, and frequency of images is specially considered. Whereas in human medicine it is common to create images of only a specific area, in animal medicine it is common to image the entire body of the patient, owing mostly to the relative size of the patient and the ease of taking whole-body x rays and/or multiple x-rays which account for most of the patient body. This further increases the value of an AI-enabled system, allowing for a total patient analysis with only a few images on common digital imaging equipment.

Furthermore, because the behavior of animal patients could be easily considered less predictable than that of human patients, anyone taking animal x-rays is incentivized to complete the process as quickly as possible. Therefore, Data. Acquisition taking place at the "Image" level and building up into "Studies" (a collection of patient images) in real time is highly desirable in animal specific systems for the purposes of visual user feedback (such as on-screen message(s) or image(s)), auditory feedback (e.g., computer "beep" or other sound), expediting medical follow up, creating predictions, or otherwise.

The medical images of patients, along with other patient data, such as date of birth, breed, the results of other tests, hospital/doctor information such as treatment dates, doctors, and other information may enter the system 110 through several general ways: 1) sent or extracted from a Picture Archiving and Communication System (PACS) or other patient records system; 2) sent as DICOM images directly from an X-ray or other imaging machine to our company's DICOM server; and/or 3) through other electronic or non-electronic means such as email, MMS, web based UI, other software input or bulk loading, fax, or paper reports.

In an embodiment, Patient Data composed of data and/or digital images are received by the Patient Data Server 120, for example, in DICOM, text, JPG, or other formats. These data and/or images may come directly over the internet from a medical imaging device 100 automatically or upon manual request, via connection to a server, or submitted or obtained through the internet, in a browser, from a mobile device, software system, or other methods. The images may be received individually (Image) or as a series of images (Study) which are multiple images of the same patient. Once Patient Data receiving 110 is complete, for example after a predetermined 30-minute period of receiving data and/or images for a specific patient has lapsed, the data and/or images are now designated as a "Patient Case" and saved 130 in the Patient Case Data Store 210. After the Patient Case is persisted, it is available for several purposes, including labeling.

Labeling Workflow

Labeling is a widely understood process for data preparation in which individual data, or groups of data, such as a Patient Medical Image or Patient Medical Case composed of one or many Patient Medical Images, is assigned one or more labels. "Dog", "Thorax", and "Cancer", are examples of labels that might be assigned to Images/Cases to indicate the presence of a dog, a thorax, or cancer. When a doctor goes through a set of Images/Cases and creates labels for the images, they are said to be performing the labeling workflow.

Labeling is directly related to the desired prediction. For example, to create a model which can predict the presence of cancer, labels of "Cancer", "No Cancer", and "Unknown", could be created to reflect the different determinations the labeling doctor assigns. These labels can be stored in a database, electronic spreadsheets, or otherwise. In one simple example, a web-based spreadsheet holds all label data, where each row indicates an image and each column a label.

Patient Images and/or Patient Cases are presented to a medical doctor or other expert who assigns one or more labels as mentioned above to identify various aspects of each Image/Case. For instance, a doctor may look at a single image and label it as "Cancer". In another example, a doctor may look at a collection of images as a Patient Case and label it as "Cancer". In another slightly different example, a doctor may look at a collection of images as a Patient Case and label it as "Cancer", while also a single image from the same case may be labeled as "Normal" because cancer is not present in this particular single image, but cancer is present in other images from the same Patient Case. In another example, a doctor labels a certain pixel or pixels of a Patient Image as "Cancer" while other pixel(s) are labeled, implicitly or explicitly, as "Non-Cancerous". In yet another example, the user might outline the area of the patient's heart on an appropriate area of an image and label it as "Heart".

Figure 2:
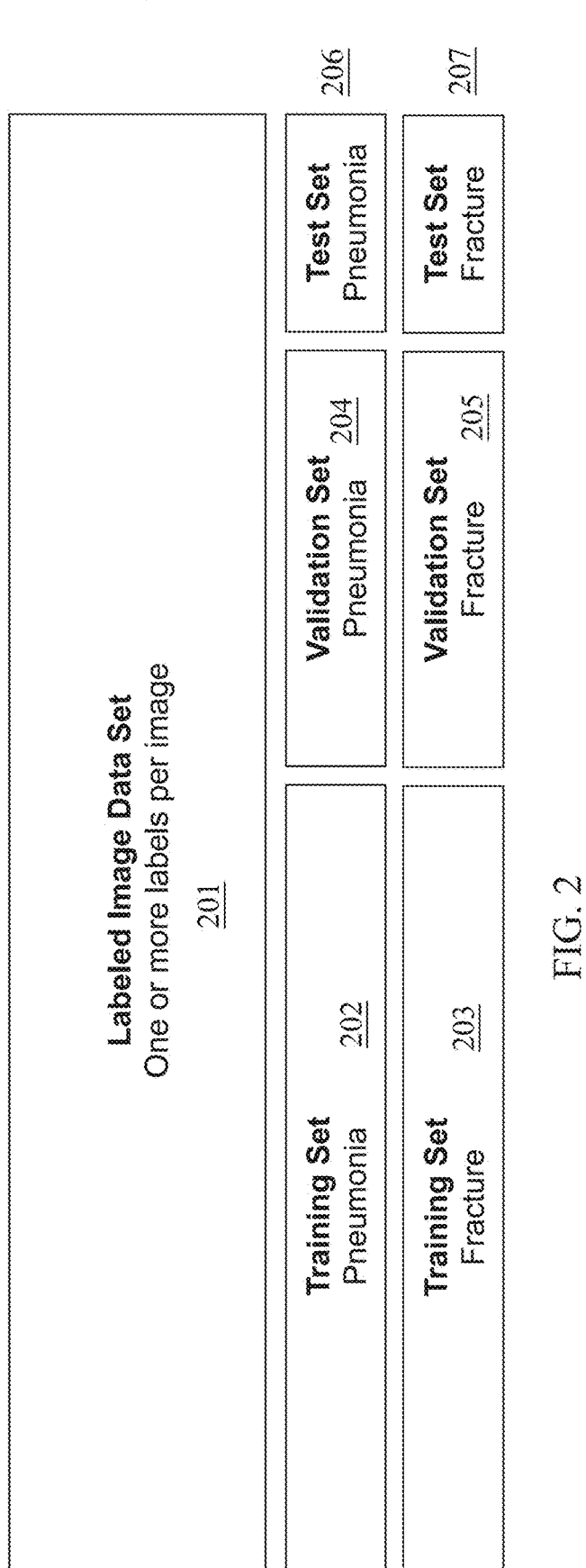
FIG. 2 is an exemplar framework for neural network training, validation and testing.

While this labeling process can be performed with any number of generalized tools (such as using standard PC folders to store images on a user's desktop alongside a spreadsheet for labels) or various labeling tools, we present a specialized user interface for medical Image/Case labeling as the Ideal Radiologist Experience (IRX) (FIG. 2). A specialized system is necessitated because labeling efficiency and quality are critical to the initial, operational, and long-term state of any model. Additionally, this addresses the time involved in labeling, the value of labeled data, and the cost of qualified and trained doctors. This specialized system creates valuable efficiencies due to the unique needs of medical labeling, and the specialized training of existing doctors, further improving clinical outcomes of any embodiment. Finally, because medical images such as X-Ray and MRI require specialized viewers for optimal interpretation by a doctor, a specialized system is necessitated to create the highest quality results.

One unique existing habit of doctors is the use of voice recording while interpreting patient images. Conventionally, while interpreting patient images, it is common practice for doctors to dictate what they are seeing, which allows the doctor to focus solely on interpretation without being distracted by simultaneous physical entry (by handwriting or typing, for example) of notes. In an AI system, the doctor should continue to have this freedom as well as the opportunity for new levels of assistance not normally available while using handwriting or tape recording, for example. Therefore, in order to maximize doctor's attention and time in this system, the doctor may use solely one input method or a combination of mouse, keyboard, and voice input to apply labels. For instance, as illustrated in FIG. 2, the doctor may see the screen and make a case evaluation by looking at the images, tags, patient history, and other data. The doctor may use voice to switch images by speaking any number of relevant commands such as, for example, "show me image 1" to enlarge an image and "show me all" to show all images. Labels can be applied or removed similarly by a command such as "no pneumonia" to remove the tag or "cardiac" to add the tag. Similarly, the actor may say "next" to advance.

All labels created and/or validated by humans or created otherwise may be persisted in the "Patient Case NN Label Database" 290 for use in the Training Set.

NN Training—Training Set Preparation

Referring to FIG. 2, before training a Neural Network, a Training Set must be prepared. Given a Labeled Data. Set 201 from the previous step, which contains multitudes of Labels of Patient Images and Patient Cases and the underlying Patient Case Data 210 itself (e.g., text, images, etc.), the system can now take various subsets of the Labeled Data Set 201 as one or more Training Sets. While the larger Labeled Data Set 201 may contain many various labels for a variety of use cases (e.g., heart, lung, etc.), in taking a subset as a Training Set the data is intentionally narrowed for a specific use case, for example to train Cancer detection by taking 100 Patient Images labeled as "Cancer" and 100 Patient Images labeled as "Normal", such that the Neural Network etc., will be able to use this data as a basis for training and building a model which can predict if a future image is "Cancer" or "Normal". In another example, a data set could be prepared as a multitude of conditions such as "Cancer", "Fracture", "Pneumonia" using 1000 Patient Images that have been labeled for all 3 conditions, and 1000 Normal Patient Images. In yet another example, the data set could be prepared as "Cancer" using 1 billion labeled Patient Images and 487,632 Normal Images. In still another example, the data set could be prepared to detect "Heart" as 400 images where the "Heart" has been labeled and 400 images containing no "Heart". In another example, the images are of animals representational of the population that will be served by the resulting system.

Through this process of narrowing the Labeled Data Set 201 into a Training Set 202, 203, different amounts and/or types of labels may be applied to varying numbers of images, often depending on availability in the medical field. This is because some conditions, such as Lung Lobe Torsion may be rarer than others such as Spondylosis (a common identification for spinal degeneration).

Concurrent with the process of developing a Training Set 202, 203, also comes the important and necessary step of creating a separate Test Set 206, 207. The Test Set 206, 207, is a collection of data, from the same set of Labeled Data 201 as the Training Set 202, 203, which is kept separate from the beginning of the process in order to have some images which are completely unseen by any neural network and therefore can be used to test the effectiveness of a particular Training Set 202, 203, as described in detail later.

The detection of some conditions may be localized, whereas others could occur throughout different parts of the body. Take for example a Cardiac condition vs a Fracture. A Cardiac condition could always be detected in the heart area so the condition could be detectable by one model only 250 and therefore require only a single Training Set. However, a Fracture could occur in many different regions of the body, and therefore it may be beneficial to create a multitude of Fracture Training Sets 203 specific to different areas of the body. Furthermore, if we want to identify body regions for understanding which area(s) of the body might need to be passed to which Fracture Model we could create another Training Set with body area labels (e.g., Thorax, Right Limb, etc.) to identify body area.

In another scenario, we may group "Cardiac" and "Enlarged Heart" into one Training Set because it could be advantageous to detect them simultaneously either for medical purposes and/or for model efficiency. In yet another scenario, we may create two training sets, a Training Set to detect "heart region"/"not heart region" and another training set for "Cardiac"/"Normal", which would be used by two models, the first determining if the relevant "heart region" area is present 250 and proceeding to predicting "Cardiac" condition 240 only if necessary.

Another intention to create a Training Set could be to detect the presence of a patient as either "dog" or "cat" or another species, so that "dog" or "cat" specific models 260 could be utilized for the detection of conditions on a per species basis. Still another reason could be to detect non-relevant images, such as CT scans or Ultrasounds, or even relevant images that do not meet qualities of alignment, lighting, etc.

To further expand the usefulness of the Training Set, it may be helpful to include non-image data, such as the patient's age or breed, categories or other identifiers, numerical representations of the patient, medical history, doctor's notes, test results, other medical record information, voice memos, machine learning (MIL) or non-ML analysis of patient data, or other non-image based patient data in the Training Set itself to better detect "Cardiac", For instance, patient age could be included to train for young dogs and old dogs, or breed could be used to account for the difference in Pitbulls vs French Bulldogs. In another example, an analysis of the previous doctor's voice notes is used to generate a scoring of 0-100 how likely the patient is to have "Cardiac" and that score 270 is included in the Training Set, alongside the images.

Training for medical imagery can take unique advantage of some preexisting medical tagging by focusing on localizing detection to one region of the body which could correspond with a particular x-ray view. For instance, in the detection of a megaesophagus condition, a Training Set prepared on only the LR (e.g., left/right side views, a medical designation, etc.) images could show significantly higher accuracy than if attempting to detect megaesophagus on any view (for instance, VD, ventrodorsal, "top" view, etc.). Each medical image, labeled by both condition and view, can then be prepared into the Training Set, by selecting from all available images for the condition, and subdividing the label by view (e.g., "MegaesophagusLR", "MegaesophagusVD", etc.). This allows for further inputs on a meta-model, which can now be used for calculating the combination of the conditions detected, the probability 270, as well as the side. Similarly, or in conjunction with this methodology, other meta-tags of the x-ray may be taken into account such as the area of the body (e.g., Thorax, Abdomen, Limb, etc.), age of the patient, or in the case of animals, the breed. Thus, a single model or multiple models could, for example, be trained on a dataset labeled MegaesophagusL-RYoung MegaesophagusLRAdult, along with tabular data containing breed.

NN Training: Preprocessing

In order to optimize the data for training, the system takes an instance of a Training Set from the previous step and preprocesses the images and/or other data, possibly applying any image cropping or segmentation via procedural code or other neural network to isolate any wanted, or remove unwanted regions, possibly applying image adjustments such as contrast or binarizations, possibly applying any flip, rotation, warp, or affine transformations, possibly scaling images to uniform sizes or different uniform sizes for different training steps, or applying other transformations such as combining multiple images into one image, or breaking down one image into multiple images, or possibly incorporating one or many of the these preprocessing steps to combinations on fractions or amalgamations of images.

At this time, the total size of the Training Set may be similarly expanded to create additional images to expand the data set by performing any or all of the above transformations. This process is known as data augmentation.

In preprocessing medical imagery, a specialized domain-specific transformation or augmentation may be applied to preprocess an image based on the type of image or use case. For instance, in the detection of fractures, it may be found beneficial to apply a preprocessing specific to the musculo-skeletal system which highlights bones and removes other visual information found to be less relevant to the detection of fractures. This preprocessing could take the form of sequential computer code or a neural network.

Lighting and rotation transformations and augmentations are particularly useful when performing preprocessing on medical images. Lighting transformation and augmentation (randomly raising or lowering the brightness/contrast of an image) helps to account for lighting differences of various real world medical imaging machines and exam conditions. Similarly, rotation transformation and augmentation (randomly rotating the image) is found to be useful in accounting for slight rotational differences in conditions present in images due to the patient's positioning on/in/relative to the medical imaging device.

NN Training: Training

The software process with or without a human operator, "trains" a neural network model (a variety of CNN, RNN, ImageNet, DenseNet, MobileNet, ResNet, SVN, for example, but not exclusively) on the preprocessed Training Set from the previous step. The Training Set may be subdivided into Train/Validate or Train/Validate/Test subsets before, after, or during preprocessing, a common best practice in the fields of statistics and machine learning.

A new neural network model is created in an initial "blank state" or may have been previously trained on other image sets such as a general set of images to pretrain the model with a basic sense of edge detection (e.g., ImageNet, etc.), or on a specific set of images such as X-rays in order to increase predictive power on specific types of images.

The neural network model can then be trained by manual or automatic process—the training may consist of one or multiple training steps, often each step having its own Learning Rate (how "fast" the neural network should learn) and Number of Epochs (iterations), during which the neural network model is "shown" the set of images and or other data from the Training subset of the Training Set, as well as the relevant Labels 290, and updates its internal model, also at each step provides some feedback as to its current prediction abilities so that the next training step can be properly performed, with the human operator or software possibly evaluating Learning Rate and/or metrics such as Accuracy, Training Loss, Validation Loss (using the Valid subset, without labels, from the Training Set), Error Rate, F1 score, and/or other metrics to determine optimal training.

The trainer or software may also include steps which train on images of different size, quality, or configuration than in previous or future steps. Outputs from each training step such as the Confusion Matrix, Top Losses, as well as evaluations of the Train/Test/and/or/Validation sets on the generated models may be taken into consideration.

After completing one or more training steps, the resulting neural network may be asked to make predictions 270 on the Test Set (from the Train/Test or Train/Validate/Test split) of the Training Set, either based on individual Patient images or collections of images, possibly as Patient Cases, in order to better evaluate how the model could perform in real world (unseen, non-Training Set) conditions.

The outputs of the Test Set can also be utilized to create Rules for the Rules Engine 230 (see Model Deployment), for example there could be a Rule that for any Patient Case, "Cardiac" must appear on 2 images contained in the Patient Case to confirm a "Cardiac" diagnosis, and therefore any cases with only a single image should not be evaluated for "Cardiac". Another example of a rule is that two neural networks, both which predict cardiac, must agree that a cardiac is present to confirm an output of "Cardiac". Another potential rule could be that a Heart needs to be detected in an image in order for a "Cardiac" prediction to be confirmed.

When the metrics of prediction are satisfactory, the neural network model and optional rules can be published to be utilized by the Model Running Server 220, possibly as part of a collection of neural networks and rules covering varying species, conditions, body regions, or other singular purposes or amalgamations.

Before or after the time of publishing, the Model Running Server may be used to provide an additional evaluation of the Test Set or of another Test Set, for instance to provide insights into how this newly created neural network improves or diminishes the overall predictive power of the collection of neural networks and rules made available to the Model Running Server, or how it performs in other simulated or real-world situation.

By virtue of adding data and conducting rigorous testing, models are designed to improve over time. This is where active learning, as referenced previously, can take place. Outputs from training may also be used to adjust the Labeled Database or Training Set, possibly with the assistance of a qualified doctor, possibly using the IRX 320, so that the process can be repeated for improved metrics such as Specificity and Sensitivity, Accuracy, Test. Set error rate, or otherwise. For instance, during training it might be determined that Patient image #5 of a Training Set was not appropriately labeled, should therefore be readjusted so that it can have a better impact on future training.

In practice, this iterative and scientific methodology is repeated hundreds or thousands or even more times in order to ascertain the correct methodology for Training Set and Test Set development, applying preprocessing, adjusting settings or parameters ("hyperparameters"), number and type of training steps, and ultimately how all the models in the system should be setup to work separately and together to create ideal results given the current desired use case such as "Detect Fracture" or "Identify Species and Detect Any of N Conditions".

Artificial Intelligence (AI) Report Server

The AI Report Server 160 performs the function of receiving new reporting requests, managing their execution by the Model Running Server 220 (for example, via a "queue"), and then performing final display (e.g., formatting as an email or document) 190 and routing logic (e.g., send it back to the requesting doctor) to deliver the appropriate formatting of a report to an appropriate receiver or receiving endpoint.

Model Running Server, Deployed Models and Rules

In any deployed AI system, it is common to have one or more models which may work together to produce a useful output. Specific to medical systems, there is nearly unlimited need to deploy an increasing number of models to provide coverage for an increasing number of conditions as well as fine grained tuning, for instance, moving from a generalized Lung model to one which is specific by breed or age, for example. In animal medical systems, this need is exacerbated by the presence of "full body" patient images, or a multitude of images which comprise nearly the entire patient body, offering opportunity to not only detect even more conditions than in humans (because of the rarity of "full body" human imaging) as well as leverage the interplay of insights in detection and decision making. For instance, while a chest x-ray may be an opportunity to detect both heart and lung conditions which may correlate, because of full body images in animals, it is advantageous to correlate a variety of conditions throughout the body, for instance accounting for gastric or skeletal conditions, in order to produce an output. Therefore, only a specialized animal medical deployment system is capable of capitalizing on the entire opportunity to assess patient condition.

In the example in FIG. 1, the Model Running Server 220 operates a multitude of neural network models which are interconnected by logical decisions, where the intermediate and final outputs are error corrected by the Rules Engine 230 at which point the Model Running Server 220 has finished execution and stores results in AI Findings Data Store 360.

The Model Running Server 220 governs execution of all Deployed Models 240, 250, 260 and Rules 230. We take a single trained neural network or collection of trained neural networks from our previous step and deploy them to a computing device such as a server, a user's local computer, a phone, or otherwise in order to make the models available for use. The Deployed Models 240, 250, 260 use new Patient Cases, Patient Images and/or other data 110 to generate predictions 270 of disease, conditions, other identifiers, or absence of, based on their respective Training Sets described above, governed by the Model Running Server 220 which calls the single or multiple models in serial, parallel, or based on if/then/else, neural network outputs, or other operation, receives the results, sends the results to the Rules Engine 230 for evaluation, and finally can deliver Report Data, usually directly back to the AI Report Server 160, via electronic means, or other means.

The Model Running Server 220 may apply data transformations and or augmentations (as described in Training Set preparation above) or other transformations or augmentations of the input images before sending the data to the Deployed Models 240, 250, 260.

Output from Deployed Models 240, 250, 260 may be used by the Model Running Server 220 to make a processing decision, such as what other Deployed Models 240, 250, 260 to send the images to for further processing, to make a clinical decision based on factors such as neural network confidence, area of identified disease, collected output values, other patient or clinical data not previously exposed to the Deployed Models 240, 250, 260, or other factors, or to make a decision to reject an image or a case based on content (for example, such as the presence of a rabbit image in an embodiment which is not designed to identify rabbit conditions).

For example, a case consisting of three X-ray images of a dog may be sent to a Deployed Model 240, 250, 260 which determines if the image is an Ultrasound or X-ray. Once it is determined that the images are indeed X-rays, each image could be sent to a Deployed Model 240, 250, 260 which predicts "Pneumonia" on 1 of the 3 images. Adding a further step in serial or parallel, the images could be identified by body region using a neural network, and once an image from the case is predicted to be a "Musculoskeletal Limb" the image may then be sent to a "Limb Fracture" model which may indicate the presence of a "Limb Fracture". These outputs ("Pneumonia" on one image, "Limb Fracture" on one image) may be evaluated by the Rules Engine 230 before a Report 190 is created.

Rules, as mentioned briefly above, are procedural or neural network decision-making tools which can be configured in myriad ways to perform a critical error correction function and therefore improve and optimize the overall quality of the outputs from the Model Running Server 220. Rules could be defined as software code to express requirements, for example, for number of images in a Patient Case, body regions of images in a Patient Case, species or breed or other pertinent information present in Patient Case, number and kind of neural network predictions for a Patient Case, or fractions, ratios, or other mathematical operations, neural network or other model, or other operations in order to error correct the output of the Neural Network.

Additionally, Rules may exist independent of a neural network and be used as intermediary steps during Model Running Server's 220 calls to Deployed Models 240, 250, 260.

Critically, this system takes advantage of the unique properties of a medical case in order to best formulate rules. Because the most common real world use case is predicting based on a multitude of images comprising a Patient Case, we are able to gather neural network outputs and other data from multiple images and use that information to create the best possible decision making necessary for Rules.

Each time a new neural network is created, such as to detect "Cancer", or if the neural network for "Cancer" is retrained, the corresponding Rule(s) can be updated to best error correct this particular instance of the "Cancer" neural network by evaluating it with respect to the Test Set. For example, if a Test Set of a "Cancer" Training Set is found to provide 10% error rate, but 50% of the errors are from Patient Cases where "Cancer" is detected on less than two images from each case, it may be possible to significantly reduce the effective error rate by creating a rule that rejects a "Cancer" diagnosis if it is detected on only one image of the Patient Case. This could, for example, mirror a real-world analysis that a doctor may not have the highest accuracy predicting cancer using a single patient image. Similarly, rather than a logical rule, a neural network-based Rule could be created to determine the optimal error-corrected outputs by training on the outputs of the Validation Set from the previous step. In this way, Rules may be optimized directly based on evaluations of the model and Test Set.

In a more expanded form, a Rules Engine 230 can take the form of a neural network or other model trained on the outputs of multiple neural networks which analyze image features and/or patient conditions and testing on existing patient cases which have been labeled at the case or both the image/case level, possibly taking into account other data sources, thereby reducing error from all other models in the system.

Figure 3:
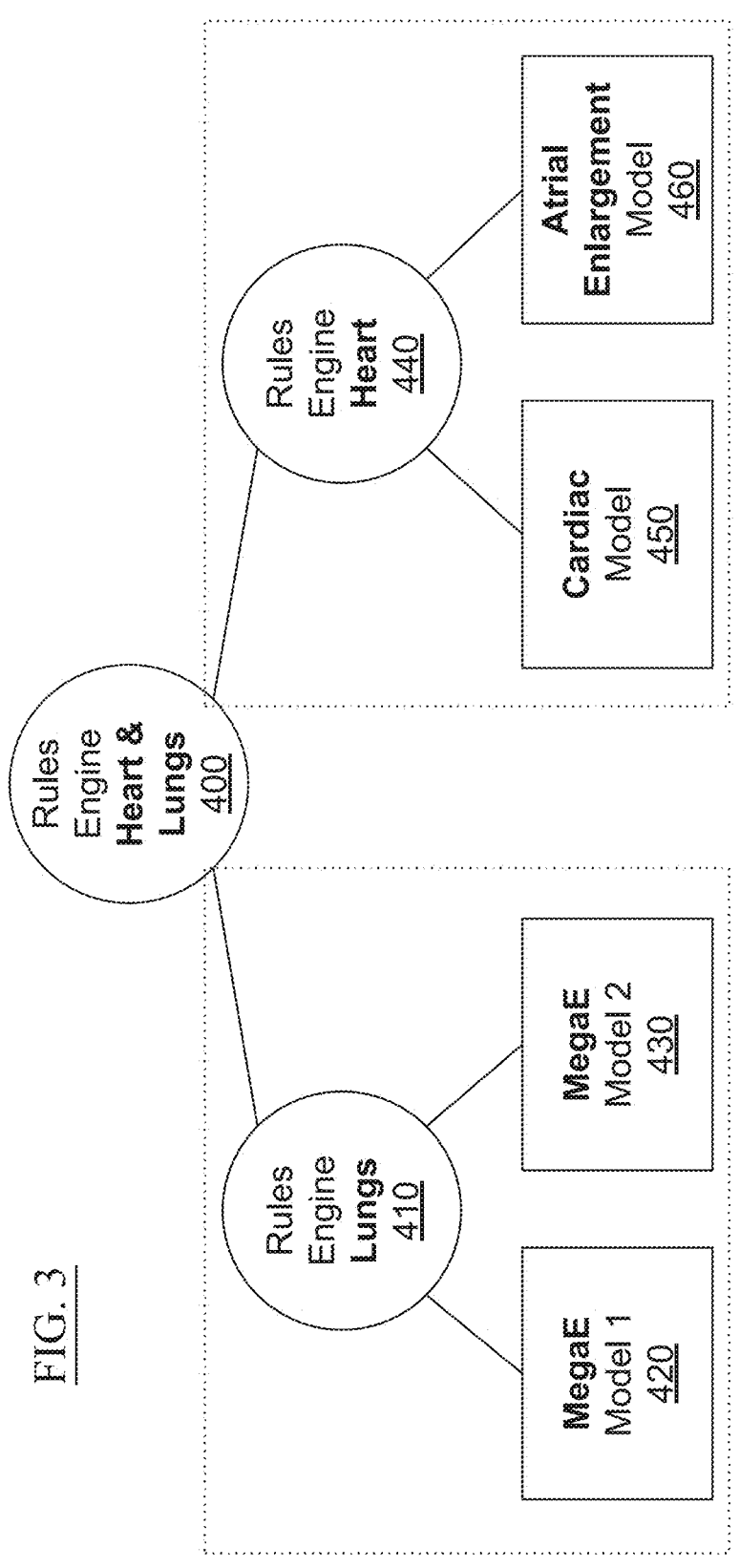
FIG. 3 illustrates an example of a multitude of models for various heart and lung conditions, with multiple Rules Engines working together.

Referring to FIGS. 1 and 3, in an embodiment, the Rules Engine 230 may take the form of multiple Rules Engines, which work in a larger decision tree of processing and may exist in either a consolidated or distributed manner. This allows for maximal improvement, as Rules Engines 230 can be flexibly deployed or updated based on the active learning progress of the system. For instance, for a single case, three rules engines could be executed: one rules engine 440 to interpret outputs from an array of heart-related neural networks 450, 460, another rules engine 410 to interpret outputs from an array of Lung-related neural networks 420, 430, and yet another rules engine 400 which interprets the outputs of the other two networks in order to form a final decision about what Heart and/or Lung conditions are determined to be present or not. Furthermore, should this example system then actively learn to the point where it needs only a single model to detect all heart and lung conditions, it could be deployed as such behind the single top level Rules Engine 230.

Outputs from the Model Running Server 220 could represent medical diagnoses, e.g., indications of disease or lack thereof, indications of other non-disease conditions, and/or other indications. For instance, one result from evaluating a Patient Case could be outputs of "Pneumonia, Normal Heart, Fracture" to indicate a Pneumonia in the Lungs, Normal Heart, and a Fracture in the Skeleton. Alternatively, for a different case and/or system configuration, the Model Running Server 220 outputs could be "NO Cancer 0.08, NO Blockage 0.634" to indicate that no Cancer nor Intestinal Blockage is present, along with the associated numerical value or metric of confidence of the prediction 270.

Generated Reduced-Multibar Reports from Computer-Assisted Interpretation

Taking outputs from the Model Running Server 220 in the previous step, a human readable, and clinically useful, report can be created from the results. This report can be useful to both medical professionals and owners to represent an interpretation of the patient's state. Therefore, it is necessary to be clear, as well as comprehensive, not only about anything that may be found to be medically relevant, but also to communicate that a variety of conditions for a patient have been checked. Furthermore, due to the large number of conditions which may be indicated by a sufficiently large embodiment of the system, such as greater than 6, the complete set of outputs must be reduced to maximize human readability. For example, given outputs from an embodiment of the system that can predict 10 different heart conditions, and a case that is found to have only normal heart conditions, all 10 heart conditions can be reduced to a single output of "heart normal".

All outputs may optionally be grouped, filtered and/or translated into text and/or still/motion graphics, audio, voice, or otherwise which allow for the conveyance of information 190 for the purposes of informing a veterinarian and/or animal owner or another actor about the findings of the Deployed. Models 240, 250, 260. This information 190 may be delivered 170 via email, SMS, MMS, mobile app notification, desktop software notification, browser notification, within a web browser, in a desktop or mobile app, by other electronic means, or otherwise and may be positioned in conjunction with other information.

For each output displayed, the confidence value or metric of the prediction or other metric may be indicated visually, possibly as a bar (hence Multibar), or alternatively as a circle, square, line, or other shape, in 2D or 3D, or numerically or graphically in proximity to at least one output having a confidence value, etc.

In one embodiment of the report 190, any conditions identified critical to care may be moved at or near the top of a report or section of the report, further improving readability by a professional in a medical situation. In one variation of this embodiment, some items may be further removed from the report if a condition has been moved to the top.

Optionally, previously defined or dynamically generated recommendations may be displayed in proximity or reference to the Multibar display, such as to communicate treatment options for a condition. This reporting may or may not accompany other common patient data or operational data such as patient name, hospital name, age, breed, etc.

In one variation 330, after a report is generated by the AI Report Server 160, but before the report is delivered to a user 190, a doctor or other actor reviews the report, possibly making modifications, adjustments, or additions before the report is sent to a user.

Medical/Imaging/PACS Transmission/Update from Computer-Assisted Interpretation

Figure 4:
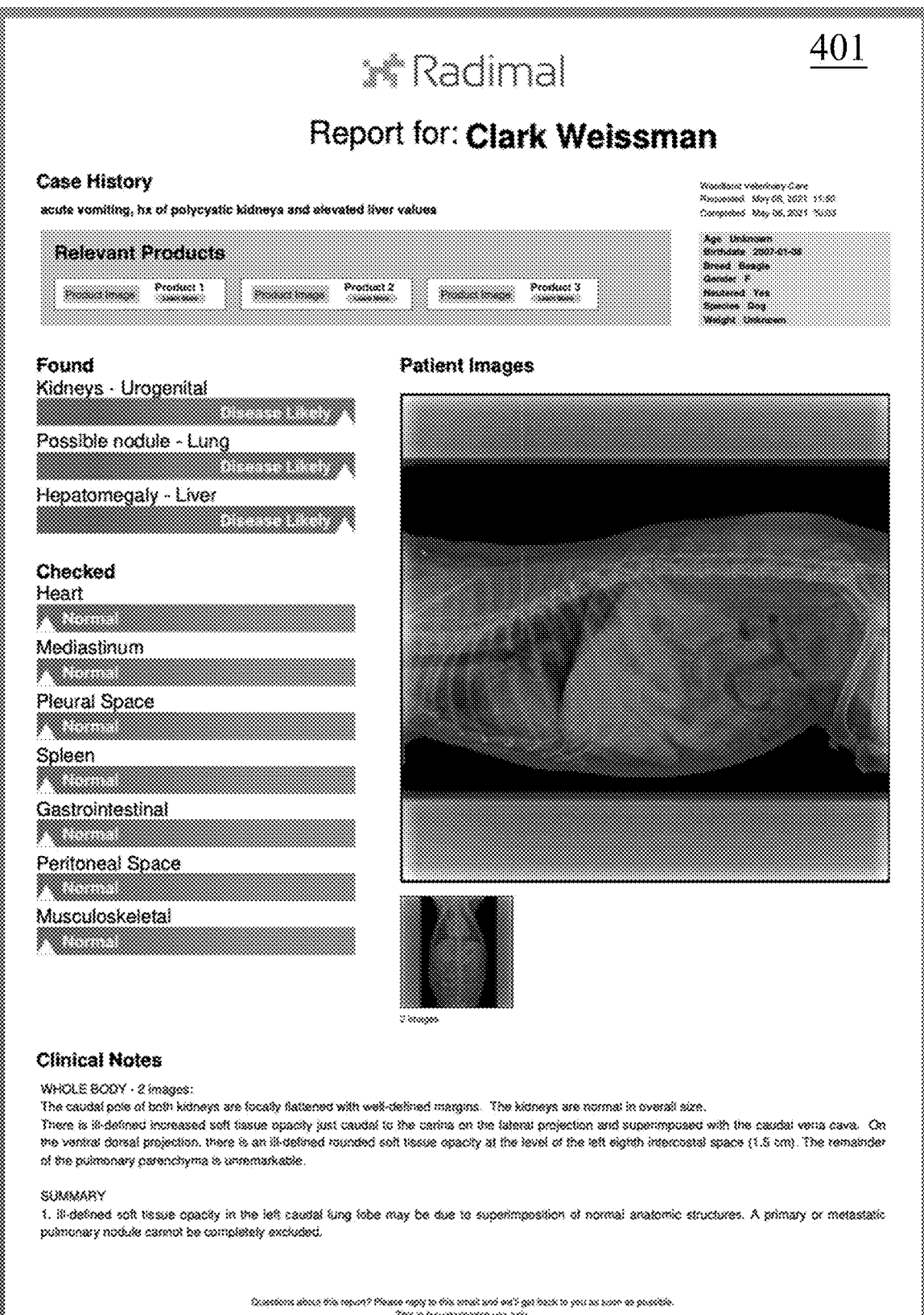
FIG. 4 illustrates an example of a Generated Reduced-Multibar Report which is a human readable conversion of neural network outputs and possibly other data, according to an embodiment of the invention.

Referring to FIG. 4, in an embodiment, generated reduced-multibar report information 401 is transmitted electronically 170 to a medical or imaging or PACS system.

Medical/Imaging/PACS Transmission/Update with Human Assist

There may be times when it is necessary to perform the transmission/update 170 with human assistance. Text, images, code, audio, or other assets may be added by a human, and/or the transmission/update 170 may be initiated by a human.

For Both Human Assisted and Computer-Assisted Transmission/Updates to Medical/Imaging/PACS Optionally, any existing or resulting information may be delivered 170 via an update over the internet to the veterinarian's computer system, for example, a patient records system, PACS system, EFilm system, or otherwise.

As part of the transmission/update 170, there may be contained an aspect which links the transmission/update and therefore the user back to the generating system and enables the user interacting with a manifestation of the report to perform actions based on the report, such as to view the same data in another way, to view other related data, or to initiate action, for example to Request Radiologist 200 for a Human-Assisted Read 340, provide feedback to a representation of an AI output, or invoke a software method which may or may not be related to the update, or otherwise. The method of enabling this interaction 200 could be for example a hyperlink in PDF, a hyperlink in HTML, Javascript or Liu. or another scripting language, or a proprietary method in the system associated with the manifestation of the report, or another method.

Request Radiologist

Optionally, after viewing a Generated Reduced-Multibar Report 190 or Medical/Imaging/PACS Update, or independently, a veterinarian, patient's owner, or another relevant actor may use a physical button, software button, software link, voice command, or phone call to request a human-assisted image interpretation 200, utilizing none, some, or all of the previous data received or generated, and/or additional images, text, voice information, or other information provided and obtained by speaking to a DACVR or another actor over the telephone, in person, or via chat.

Ideal Radiologist Experience—IRX (FIG. 2)

Figure 5:
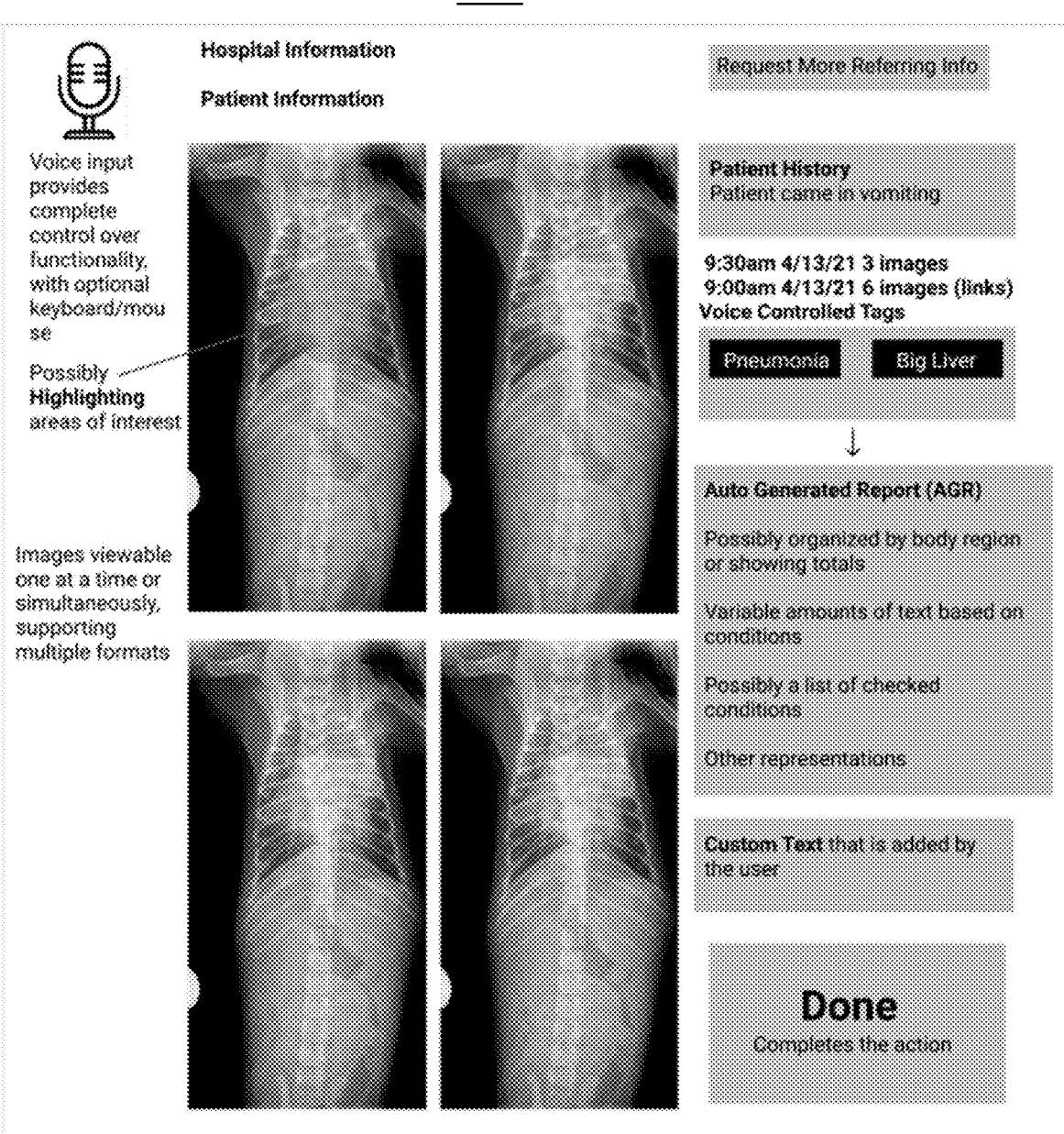
FIG. 5 illustrates an example Ideal Radiologist Experience (IRX), a user interface that enables an actor to be assisted by Artificial Intelligence (AI) during case interpretation and labeling, according to an embodiment of the invention.

Referring to FIGS. 2 and 5, FIG. 5 shows one example of a user interface 500 for reading images which incorporates hands free voice input, AI assistance, and outputs ready for doctors, owners, patients, data, and machine learning systems. In an embodiment, for the purpose of human-assisted case interpretation 340 following a Request Radiologist 200 step, and/or for the previously mentioned purpose of Labeling Workflow 310, a medical doctor or another expert may be presented with a user interface (FIG. 2) which integrates all known information for the patient, images, including neural network outputs and/or other generated information, in a way which allows the actor to operate the process completely by voice. There may be features which otherwise enable functionality via mouse, keyboard, or other input, but the actor is able to provide a complete human-assisted image interpretation 340 and/or labeling 310 via voice, including the ability to switch between images/cases/patients or provide other higher-level functionality so as to process a queue or workflow of images, patients, or cases. The adding/removal of labels via the IRX 320 during the Human Assisted Report 350 generation will trigger the IRX Auto Generated. Report (IRX AGR).

The IRX AGR creates efficiency by assisting the user in the "writing" of the written section of the report where, traditionally, a doctor must provide specific findings, judgements, perspectives, insights, or any other information deemed useful or relevant by the doctor. Rather than needing to write this section from scratch, IRX AGR uses the case and image ML outputs, patient information, and a database of recommendations prewritten for common conditions to create a report, either partially or in its entirety which could vary in consent style based on preference, patient type, present conditions, etc.

The IRX AGR can be generated by user interaction as mentioned above. For example, if a doctor speaks "Fracture" to identify that the current case contains a fracture, then the IRX AGR could automatically assist the doctor by pre-filling the report with the text "There is a fracture present". In another example, if the doctor labels the case as "Food", the IRX AGR could automatically pre-populate "Material in the stomach is likely food". Various labels can be selected or deselected by the IRX user to modify the pre-populated text.

The doctor may then add to, delete, or edit the AGR with custom text, images, or other media, for any of various reasons such as to comment specifically on a condition or clarify the AGR. The actor can speak a command such as "done" at any time to be automatically moved to the next case.

In one embodiment, the IRX 320 allows the doctor to read cases for either Labeling 310 or Human Assisted Report 340 purposes ad infinitum, for as many cases as there are present or available or in need in the queue. This feature can radically increase the throughput of radiologists and other specialists.

While this AGR is primarily intended as an intermediate state for a doctor to adjust as needed, the IRX AGR can also be generated without any human interaction, based on any labels which may have been applied previously, for instance electronically. For example, Image/Case may be pre-labeled by an existing neural network, and therefore the AGR could be created without human interaction. Note that any of the functionality described above may be localized or distributed in any combination across one or more data collectors, one or more computing devices, one or more servers, etc. Animal Product Recommendations Based on Findings:

Germane to the moment where the owner of an animal patient receives a physical or digital representation of a Generated Reduced-Multibar Report 190 following application of the aforementioned system, for instance during a routine medical exam by a veterinarian at a veterinary hospital, is the opportunity to provide not only medical advice from the veterinarian, but also health and lifestyle product recommendations.

Animal product recommendations may be best delivered in an automated means by a program such as sequential code or a neural network model that creates recommendations based on for example ML outputs and or other patient data such as breed, age, other text or numerical data, past test results, images such as X-ray or MRI, or any other information related to the patient. These results generated by the Product Relevance Model 180 can be displayed as part of, or side by side, or separately from the Generated Reduced-Multibar Report 190, for example presented in a software application, email, or other means. Animal products may be presented with or without imagery or, in digital format, with or without hyperlinks or other associated actions such as to "learn more" or "buy now". See FIG. 4 for one possible embodiment of product recommendations. This is useful to owner, patient, and vet for helping with the purchase of key animal product items such as food, treats, medication, vitamins, supplements, hair and fur products, other care products, comfort and lifestyle items such as beds, pillows, blankets, collars, clothes, toys or other items which intend the animal's attention, treatment options such as appointments, consultations, referrals, grooming or otherwise, or other general or specialty products and/or services which may be available. For example, a patient identified with a heart condition, a heart healthy food brand and a variety of toys for exercise could be recommended. In another example, a patient identified as young and healthy may be recommended a flea collar but in a further, more illustrative example, a flea collar may not be recommended by the Product Relevance Model 180 if the machine learning outputs and/or patient data and/or other data (described in detail above) indicate that the patient may be pregnant, nursing, senior, or otherwise infirm, because flea collars are not generally recommended for such patients. In one variation, the cost and/or any offers available for the products may be taken into account when determining which and how to display items.

In an embodiment, an apparatus comprises a processor and is configured to perform any of the foregoing methods. In another embodiment, a non-transitory computer readable storage medium, storing software instructions, which when executed by one or more processors cause performance of any of the foregoing methods. Note that, although separate embodiments are discussed herein, any combination of embodiments and/or partial embodiments discussed herein may be combined to form further embodiments.

5.0 Implementation Mechanisms—Hardware Overview

According to an embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 6:
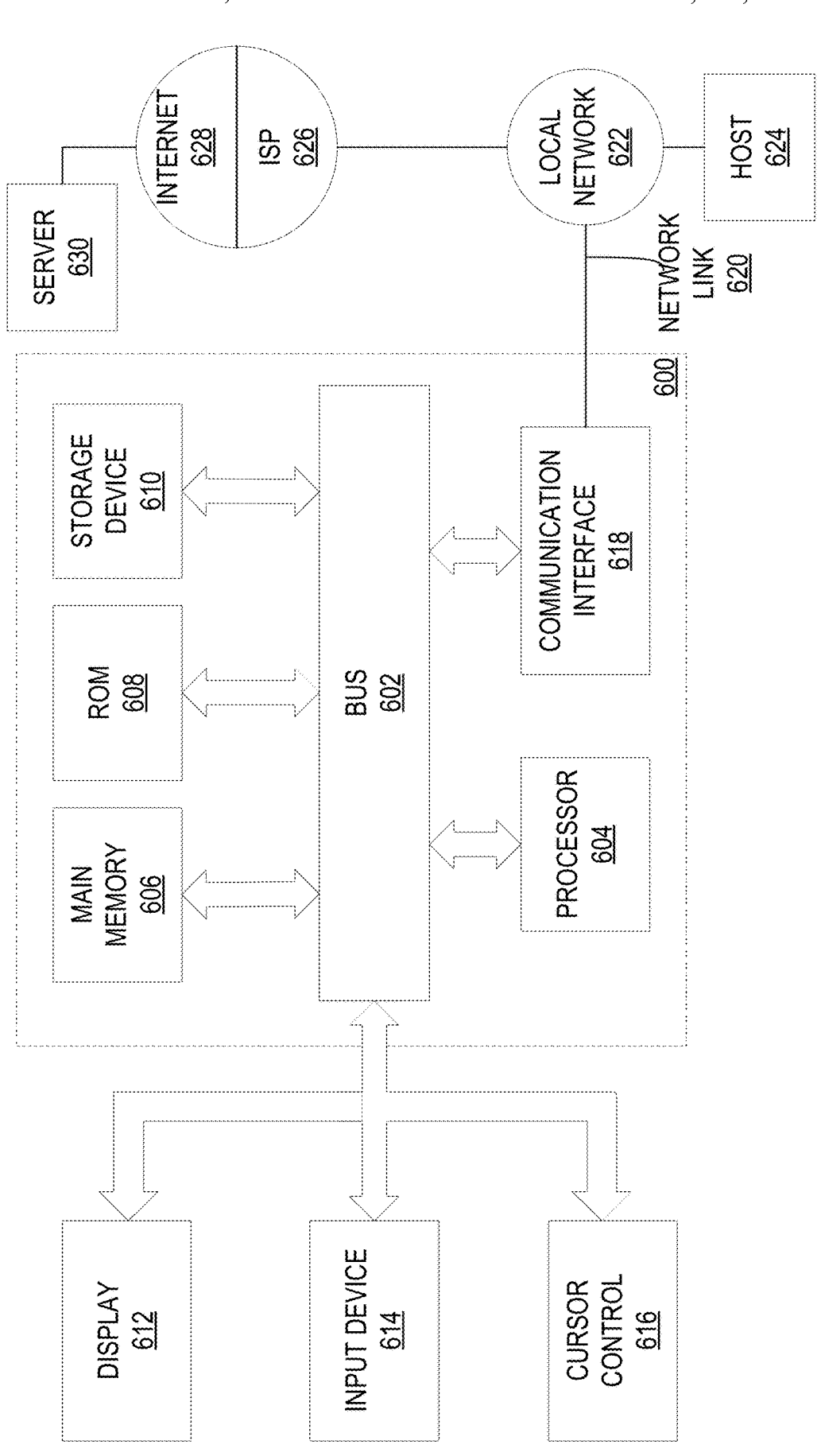
FIG. 6 illustrates a computer system upon which an embodiment may be implemented.

For example, FIG. 6 is a block diagram that illustrates a computer system 600 upon which an embodiment may be implemented. Computer system 600 includes a bus 602 or other communication mechanism for communicating information, and a hardware processor 604 coupled with bus 602 for processing information. Hardware processor 604 may be, for example, a general purpose microprocessor.

Computer system 600 also includes a main memory 606, such as a random access memory (RAM) or other dynamic storage device, coupled to bus 602 for storing information and instructions to be executed by processor 604. Main memory 606 also may be used for storing temporary variables or other intermediate information during execution of instructions to be executed by processor 604. Such instructions, when stored in non-transitory storage media accessible to processor 604, render computer system 600 into a special-purpose machine that is customized to perform the operations specified in the instructions.

Computer system 600 further includes a read only memory (ROM) 608 or other static storage device coupled to bus 602 for storing static information and instructions for processor 604. A storage device 610, such as a magnetic disk, optical disk, or solid-state drive is provided and coupled to bus 602 for storing information and instructions.

Computer system 600 may be coupled via bus 602 to a display 612, such as a cathode ray tube (CRT), for displaying information to a computer user. An input device 614, including alphanumeric and other keys, is coupled to bus 602 for communicating information and command selections to processor 604. Another type of user input device is cursor control 616, such as a mouse, a trackball, or cursor direction keys for communicating direction information and command selections to processor 604 and for controlling cursor movement on display 612. This input device typically has two degrees of freedom in two axes, a first axis (e.g., x) and a second axis (e.g., y), that allows the device to specify positions in a plane.

Computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the techniques herein are performed by computer system 600 in response to processor 604 executing one or more sequences of one or more instructions contained in main memory 606. Such instructions may be read into main memory 606 from another storage medium, such as storage device 610. Execution of the sequences of instructions contained in main memory 606 causes processor 604 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 610. Volatile media includes dynamic memory, such as main memory 606. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 602. Transmission media can also take the form of acoustic or light waves, such as those generated during radio-wave and infra-red data communications.

Various forms of media may be involved in carrying one or more sequences of one or more instructions to processor 604 for execution. For example, the instructions may initially be carried on a magnetic disk or solid-state drive of a remote computer. The remote computer can load the instructions into its dynamic memory and send the instructions over a telephone line using a modem. A modem local to computer system 600 can receive the data on the telephone line and use an infra-red transmitter to convert the data to an infra-red signal. An infra-red detector can receive the data carried in the infra-red signal and appropriate circuitry can place the data on bus 602. Bus 602 carries the data to main memory 606, from which processor 604 retrieves and executes the instructions. The instructions received by main memory 606 may optionally be stored on storage device 610 either before or after execution by processor 604.

Computer system 600 also includes a communication interface 618 coupled to bus 602. Communication interface 618 provides a two-way data communication coupling to a network link 620 that is connected to a local network 622. For example, communication interface 618 may be an integrated services digital network (ISDN) card, cable modem, satellite modem, or a modem to provide a data communication connection to a corresponding type of telephone line. As another example, communication interface 618 may be a local area network (LAN) card to provide a data communication connection to a compatible LAN. Wireless links may also be implemented. In any such implementation, communication interface 618 sends and receives electrical, electromagnetic or optical signals that carry digital data streams representing various types of information.

Network link 620 typically provides data communication through one or more networks to other data devices. For example, network link 620 may provide a connection through local network 622 to a host computer 624 or to data equipment operated by an Internet Service Provider (ISP) 626. ISP 626 in turn provides data communication services through the world wide packet data communication network now commonly referred to as the "Internet" 628. Local network 622 and Internet 628 both use electrical, electromagnetic or optical signals that carry digital data streams. The signals through the various networks and the signals on network link 620 and through communication interface 618, which carry the digital data to and from computer system 600, are example forms of transmission media.

Computer system 600 can send messages and receive data, including program code, through the network(s), network link 620 and communication interface 618. In the Internet example, a server 630 might transmit a requested code for an application program through Internet 628, ISP 626, local network 622 and communication interface 618.

The received code may be executed by processor 604 as it is received, and/or stored in storage device 610, or other non-volatile storage for later execution.

6.0 Extensions and Alternatives

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the embodiments, and what is intended by the applicants to be the scope of the embodiments, is the literal and equivalent scope of the set of claims that issue from this application, in the specific form in which such claims issue, including any subsequent correction.

In drawings, various system components are depicted as being communicatively coupled to various other components by arrows. These arrows illustrate only certain examples of information flows between the components of the depicted systems. Neither the direction of the arrows nor the lack of arrow lines between certain components should be interpreted as indicating the absence of communication between the certain components. Indeed, each component of the depicted systems may feature an open port, API, or other suitable communication interface by which the component may become communicatively coupled to other components of the depicted systems as needed to accomplish any of the functions of the systems described herein.

What is claimed is:

1. A method, comprising:
creating a training set for one or more neural network models using a set of medical images for a representational set of animals, the medical images include case specific medical images and normal, associated, medical images, each medical image having one or more descriptive labels relating to desired analysis predictions;
the creating the training set comprises preprocessing the set of medical images using one or more transformations or augmentations on each medical image in the set of medical images to isolate desired regions or remove unwanted regions of the medical image;

training one or more neural network models using the training set, the one or more neural networks determine if an input image is normal or indicates a case condition;

generating a set of results for a set of input medical images using the one or more neural network models;

processing the set of results using one or more rules engines to apply an error correction to the set of results to improve an overall quality of the set of results, the one or more rules engines determine whether a case condition prediction in the set of results is within an acceptable error rate based on the set of input medical images, the one or more rules engines are trained on outputs from a validation set to determine optimized error corrected results;

processing the processed set of results to communicate, for a specific delivery method, case predictions that include one or more medical diagnoses.

2. The method as recited in claim 1, wherein the case predictions include one or more animal product recommendations based on the processed set of results.

3. The method as recited in claim 1, wherein the processing the processed set of results further comprises:

generating a confidence metric for at least one of the one or more medical diagnoses;

displaying the confidence metric in proximity to the at least one of the one or more medical diagnoses having a generated confidence metric.

4. The method as recited in claim 1, wherein the processing the processed set of results further comprises:

generating a confidence metric for at least one of the one or more medical diagnoses;

graphically displaying the confidence metric in proximity to the at least one of the one or more medical diagnoses having a generated confidence metric.

5. The method as recited in claim 1, wherein the processing the processed set of results further comprises:

generating a confidence metric for the one or more medical diagnoses;

graphically displaying the confidence metric of the one or more medical diagnoses having a generated confidence metric.

6. The method as recited in claim 1, wherein the processing the processed set of results further comprises:

identifying a medical diagnosis of the one or more medical diagnoses as critical to care;

wherein the report places the medical diagnosis at or near the top of a section of the report based on the identification that the medical diagnosis is critical to care.

7. The method as recited in claim 1, wherein the case predictions include one or more treatment options based on the processed set of results.

8. One or more non-transitory computer-readable storage media, storing one or more sequences of instructions, which when executed by one or more processors cause performance of:

creating a training set for one or more neural network models using a set of medical images for a representational set of animals, the medical images include case specific medical images and normal, associated, medical images, each medical image having one or more descriptive labels relating to desired analysis predictions;

the creating the training set comprises preprocessing the set of medical images using one or more transformations or augmentations on each medical image in the set of medical images to isolate desired regions or remove unwanted regions of the medical image;

training one or more neural network models using the training set, the one or more neural networks determine if an input image is normal or indicates a case condition;

generating a set of results for a set of input medical images using the one or more neural network models;

processing the set of results using one or more rules engines to apply an error correction to the set of results to improve an overall quality of the set of results, the one or more rules engines determine whether a case condition prediction in the set of results is within an acceptable error rate based on the set of input medical images, the one or more rules engines are trained on outputs from a validation set to determine optimized error corrected results;

processing the processed set of results to communicate, for a specific delivery method, case predictions that include one or more medical diagnoses.

9. The one or more non-transitory computer-readable storage media as recited in claim 8, wherein the case predictions include one or more animal product recommendations based on the processed set of results.

10. The one or more non-transitory computer-readable storage media as recited in claim 8, processing the processed set of results further comprises:

generating a confidence metric for at least one of the one or more medical diagnoses;

displaying the confidence metric in proximity to the at least one of the one or more medical diagnoses having a generated confidence metric.

11. The one or more non-transitory computer-readable storage media as recited in claim 8, wherein the processing the processed set of results further comprises:

generating a confidence metric for at least one of the one or more medical diagnoses;

graphically displaying the confidence metric in proximity to the at least one of the one or more medical diagnoses having a generated confidence metric.

12. The one or more non-transitory computer-readable storage media as recited in claim 8, wherein the processing the processed set of results further comprises:

generating a confidence metric for the one or more medical diagnoses;

graphically displaying the confidence metric of the one or more medical diagnoses having a generated confidence metric.

13. The one or more non-transitory computer-readable storage media as recited in claim 8, wherein the processing the processed set of results further comprises:

identifying a medical diagnosis of the one or more medical diagnoses as critical to care;

wherein the report places the medical diagnosis at or near the top of a section of the report based on the identification that the medical diagnosis is critical to care.

14. The one or more non-transitory computer-readable storage media as recited in claim 8, wherein the case prediction include one or more treatment options based on the processed set of results.

15. An apparatus, comprising:

one or more hardware processors; and a memory storing instructions, which when executed by the one or more processors, cause the one or more processors to:

create a training set for one or more neural network models using a set of medical images for a representational set of animals, the medical images include case specific medical images and normal, associated, medical images, each medical image having one or more descriptive labels relating to desired analysis predictions;

the create the training set comprises preprocessing the set of medical images using one or more transformations or augmentations on each medical image in the set of medical images to isolate desired regions or remove unwanted regions of the medical image;

train one or more neural network models using the training set, the one or more neural networks determine if an input image is normal or indicates a case condition;

generate a set of results for a set of input medical images using the one or more neural network models;

process the set of results using one or more rules engines to apply an error correction to the set of results to improve an overall quality of the set of results, the one or more rules engines determine whether a case condition prediction in the set of results is within an acceptable error rate based on the set of input medical images, the one or more rules engines are trained on outputs from a validation set to determine optimized error corrected results;

process the processed set of results to communicate, for a specific delivery method, case predictions that include one or more medical diagnoses.

16. The apparatus as recited in claim 15, wherein the case predictions include one or more animal product recommendations based on the processed set of results.

17. The apparatus as recited in claim 15, wherein the process the processed set of results further comprises:

generate a confidence metric for the one or more medical diagnoses;

graphically display the confidence metric of the one or more medical diagnoses having a generated confidence metric.

\* \* \* \* \*